(12) United States Patent
Kleyman et al.

(10) Patent No.: US 12,268,849 B2
(45) Date of Patent: Apr. 8, 2025

(54) SYRINGE PLUNGER FINGER RING STRUCTURES

(71) Applicants: Gennady I Kleyman, Brooklyn, NY (US); Alexander Merson, Brooklyn, NY (US)

(72) Inventors: Gennady I Kleyman, Brooklyn, NY (US); Alexander Merson, Brooklyn, NY (US)

(73) Assignee: Alger & Klemer, LLC, Brooklyn, NY (US)

( * ) Notice: Subject to any disclaimer, the term of this patent is extended or adjusted under 35 U.S.C. 154(b) by 0 days.

(21) Appl. No.: 18/241,462

(22) Filed: Sep. 1, 2023

(65) Prior Publication Data

US 2023/0405231 A1 Dec. 21, 2023

Related U.S. Application Data

(62) Division of application No. 17/228,797, filed on Apr. 13, 2021, now Pat. No. 11,779,707.

(51) Int. Cl.
*A61M 5/31* (2006.01)

(52) U.S. Cl.
CPC ........ *A61M 5/3137* (2013.01); *A61M 5/3148* (2013.01); *A61M 2005/3139* (2013.01); *A61M 2210/0637* (2013.01)

(58) Field of Classification Search
CPC .............. A61M 5/3137; A61M 5/3148; A61M 2005/3139; A61M 2205/586
See application file for complete search history.

(56) References Cited

U.S. PATENT DOCUMENTS

2009/0093787 A1\* 4/2009 Barbour .............. A61M 5/3137
604/207

\* cited by examiner

*Primary Examiner* — James D Ponton
*Assistant Examiner* — Hong-Van N Trinh

(57) ABSTRACT

A syringe finger ring and finger ring inserts, that in various embodiments, provides or connects to a syringe that comprises a syringe body capable of having a volume of material therein and a plunger disposed to enter the syringe body and dispense material from the syringe body by movement of plunger, and a novel a finger ring related structures having an open area and connected, by various structures, to the plunger adapted to receive a finger within the finger ring open area, including a spacer of various embodiments inserted within the open area to selectively reduce the open area and provide more controllable engagement of the syringe plunger by the operator finger in distal and proximal strokes.

3 Claims, 2 Drawing Sheets

SYRINGE PLUNGER FINGER RING STRUCTURES

Priority is claimed on Non-Provisional patent application Ser. No. 17/228,797 filed 13 Apr. 2021, Non-Provisional patent application Ser. No. 17/137,490 filed 30 Dec. 2020, entitled Syringe Plunger Finger Ring Structures and Provisional Patent Application No. 63/071,409 filed 28 Aug. 2020, entitled Adjustable Ring Structure For Dental Syringe.

FIELD OF THE INVENTION

The present invention relates to syringes in particular, to conventional and dental syringes having finger receptacle to better engage operator finger to facilitate comfortable use of the syringes.

BACKGROUND OF THE INVENTION

Conventional and dental syringe used requires skilled and confident, accurate operation (e.g. a controlled compression of a syringe plunger) and simultaneous precise control of the needle location and depth. Moreover, it is very important to precisely accomplish both the distal (injecting) stroke, e.g. to determine whether the needle is in a blood vessel, and the proximal (aspirating) stroke. These qualities are absolutely necessary in cosmetic procedure applications (injection of Botox, fillers etc) and in dental procedures. Existing conventional and dental syringes typically have limited plunger ring surfaces. This drawback makes it hard to operate and hard to control the dispensing of syringe content. It is also very important to emphasize that the plunger ring surfaces of existing syringes don't accommodate the variety of finger sizes, and don't have any structure to enhance the operation itself or to control of syringes by the user.

SUMMARY OF THE INVENTION

Disclosed is an ergonomically improved conventional and dental syringe including adjustable ring structure that substantially surround the operator finger with portions of the syringe member that receives an operator finger, which facilitates to operate the plunger conveniently and more controllably to accomplish both the distal (injecting) stroke and the proximal (aspirating) stroke.

In various embodiments, the present invention provides or connects to a syringe that comprises a syringe body capable of having a volume of material therein and a plunger disposed to enter the syringe body and dispense material from the syringe body by movement of plunger, and a novel finger ring and related structures having an open area and connected to the plunger adapted to receive a finger within the finger ring open area, including a spacer of various embodiments inserted within the open area to selectively reduce the open area and provide more controllable engagement of the syringe plunger by the operator finger.

Those embodiments make the syringe significantly more easy, predictable, and controllable to use with both the distal (injecting) stroke and the proximal (aspirating) stroke. The result is a syringe and syringe attachment(s) which enables a reliable and controlled aspiration maneuver and to perform delicate but routine actions, e.g. to test for the presence of blood indicating that a blood vessel has been penetrated, and other critical operations, easily and controllably with one hand.

BRIEF DESCRIPTION OF THE DRAWINGS AND POSITIONS

These and further novel features of the present invention are better understood by taking the following Drawing figures together with the Detailed Description, wherein.

DETAILED DESCRIPTION

Figure 1:
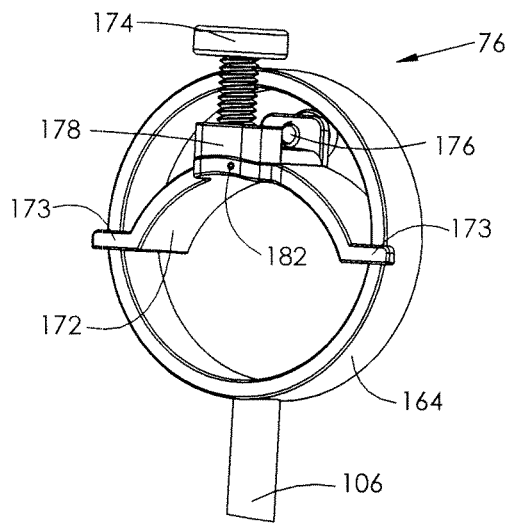
FIG. 1 is an isometric view of ring assembly of an embodiment.
Figure 2:
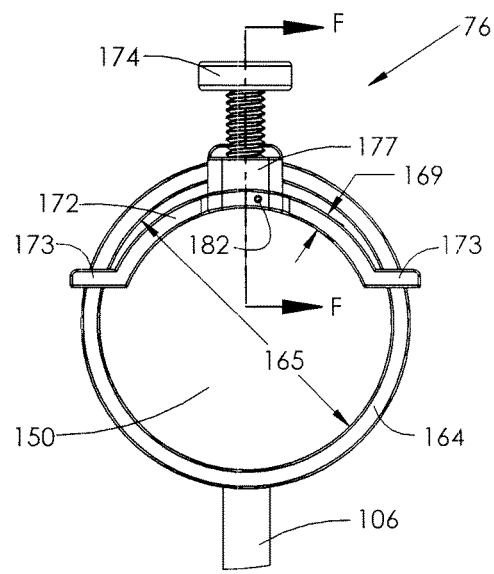
FIG. 2 is a front view of ring assembly of an embodiment.
Figure 3:
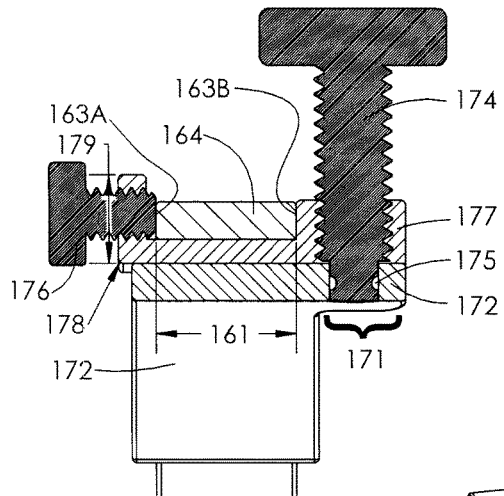
FIG. 3 is a sectional view F-F taken of the embodiment of FIG. 2.
Figure 4:
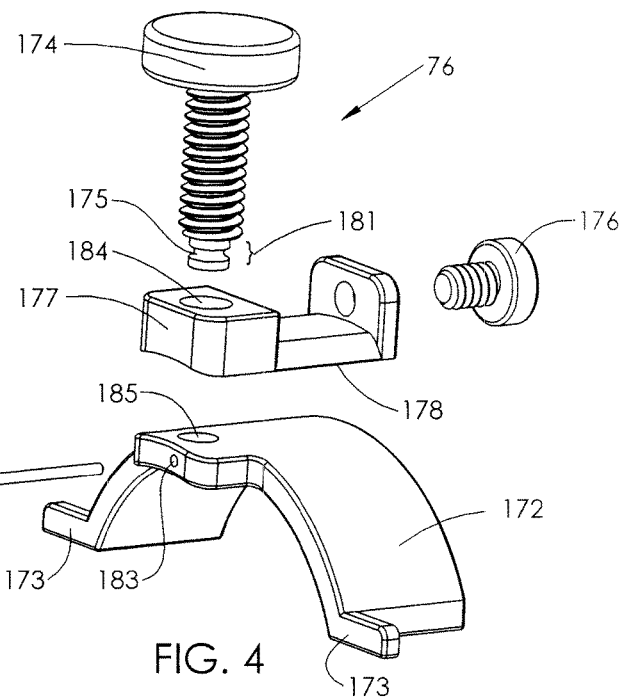
FIG. 4 is an exploded view of insert assembly of the embodiment.

An embodiment 76 is shown in FIGS. 1-4, that includes a screw 174 adjustment of an attached insertable inner spacing member comprising a curved member 172 having selected thickness 169 and is adjustable relative to an a corresponding threaded holding block 178. The holding block is retained within the finger ring annular member 164 open area 150. The finger ring 164 has a radial dimension 165 extending across the open area 150. The curved spacing member 172 retaining holding block 178 is retained to the finger ring 164 by a holding block retaining screw 176. The screw 176 engages and provides compression attachment force to a lateral edge 163A of the finger ring annular member 164 (which annular member 164 is connected to plunger shaft 106,) across the finger ring 164 longitudinal width 161 and to the opposing edge 163B against holding block 178 threaded shoulder 177. The compression attachment force across finger ring 164 longitudinal width is substantially perpendicular to the radial dimension 165. Holding block 178 has a radial dimension 179. The lateral movement (in the direction of longitudinal width 161, FIG. 3) of ends of the curved member 172 is limited by radially outward extending members or 'ears' 173 attached to one side of curved member 172 to allow insertion of the assembly of the holding block 178, screw 174, and curved member 172 into the open area 150 of the annular member 164. As shown in FIG. 3 cross-section F of FIG. 2, and exploded view of FIG. 4, the screw end 181 received into lateral extension 171 opening 185, having an circumferential recess 175, is captured by a pin 182 inserted into a curved member 172 lateral extension 171 hole 183 that is dis-posed sufficiently offset from the center of the lateral extension 171 opening 184 to per-mit pin 182 to tangentially engage the screw annular recess 175 to retain the screw 174 within the lateral extension 171 hole 183, yet permit rotation that allows the screw 174 to move through threaded shoulder 177 by rotation of the screw 174 causing the curved member 172 to advance into (or retract from) the open area to 'fit' the ring 164 to a particular finger. The curved member 172 is moved inward into the open area 150 and retained there by rotation of the screw 174 and limited in lateral motion by the ears 173, providing a close fitting to and retention by a finger inserted into the open area 150.

Figure 5:
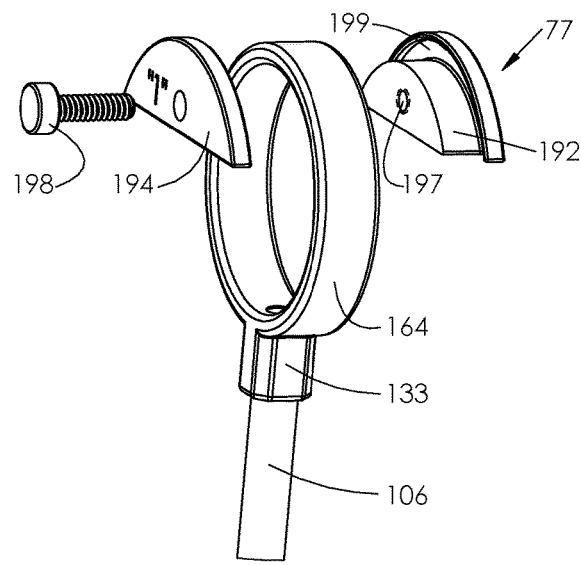
FIG. 5 is an exploded view of inserts assembly with the ring of an alternate embodiment.
Figure 6:
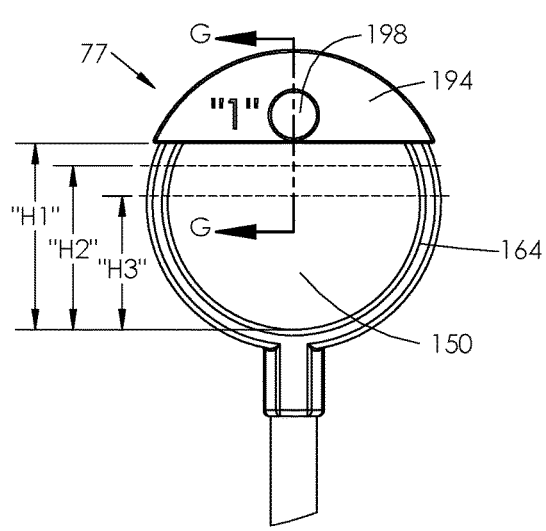
FIG. 6 is a front elevation view of inserts assembled with the ring of the alternate embodiment.
Figure 7:
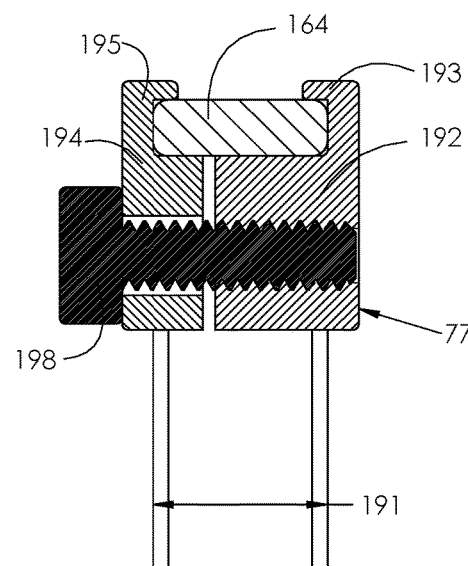
FIG. 7 is a sectional view G-G taken from FIG. 6 of the alternate embodiment.

An alternate embodiment 77 is shown in FIGS. 5-7 that comprises the annular member 164 connected to a syringe plunger shaft 106 via a shoulder 133 and has a lateral width 191, around which facing spacers 192, 194 are applied to together grip the annular member 164 when a screw 198 engages a threaded opening 197 (or other device) draws the spacers 192, 194 together and apply a compression force to the annular member 164. Typically, the facing spacers 192, 194 form a recess e.g. 199, by radially extending members 193, 195 that extend radially past, and as shown in cross section G of FIG. 7, partially surround the annular member 164. According to embodiments of the present invention, spacers 192, 194 may have a larger inwardly facing dimension to intrude further into the open area 150 to provide different interior spacings, e.g. H1, H2, H3, etc. as desired.

The components of the rigid or semi-rigid embodiments described herein can be fabricated by injection molding from different plastics such as Polypropylene, ABS, Polycarbonate or other materials that can be formed and function as described herein. Further embodiments, modifications and substitutions by one of ordinary skill in the art are within the scope of the present invention which is not limited except according to the claims as follows.

What is claimed is:

1. An apparatus attachable to a syringe finger ring having an open area within the syringe finger ring and connected to a syringe plunger having a plunger shaft axis extending radially outward from the syringe finger ring, the syringe finger ring having a radial dimension extending across said open area, the apparatus comprising:
   a spacing member having a surface disposed within said open area to provide reduction in said radial dimension; and
   a retaining member, enabling said spacing member to be retained on said syringe finger ring within said open area, wherein
   said retaining member comprises
      a holding block engaging said syringe finger ring, and
      an adjustment member disposed to adjustably connect said spacing member and said holding block and provide adjustable movement of said spacing member along said radial dimension within said open area.

2. The apparatus of claim 1, wherein said adjustment member comprises a screw and said holding block includes a threaded shoulder to receive said screw disposed to move said spacing member toward said open area.

3. An apparatus attachable to a syringe finger ring having an
   open area within the syringe finger ring and connected to a syringe plunger having a plunger shaft axis extending radially outward from the syringe finger ring, the syringe finger ring having a radial dimension extending across said open area, the apparatus comprising:
   a spacing member having a surface disposed within said open area to provide reduction in said radial dimension; and
   a retaining member, enabling said spacing member to be retained on said syringe finger ring within said open area, wherein,
      the spacing member comprises a segment member having a curved surface, curved in a first dimension, and having a selected thickness, and
      the retaining member comprises an attachment member retained to said segment member and is disposed to provide compression attachment force to said syringe finger ring perpendicular to said radial dimension.

* * * * *